United States Patent [19]

Jozefonvicz et al.

[11] Patent Number: 4,755,379

[45] Date of Patent: Jul. 5, 1988

[54] POLYMERS SUBSTITUTED BY GROUPS CONFERRING ANTI-COAGULANT PROPERTIES ON THEM, PROCESS FOR THEIR PREPARATION, ARTICLES AND COMPOSITIONS MADE THEREFROM AND USES THEREOF

[75] Inventors: Marcel Jozefonvicz; Jacqueline Jozefonvicz, both of 65, 2ème Avenue, Lamorlaye, France, 60260; Christine Fougnot, 85, Rue Marcel Grandcoing, Villetaneuse, France, 93430; Monique Mauzac, Neuilly sur Seine, France

[73] Assignees: Jacqueline Jozefonvicz; Marcel Jozefonvicz, both of Lamorlaye; Christine Fougnot, Villetaneuse, all of France

[21] Appl. No.: 781,203

[22] Filed: Sep. 27, 1985

Related U.S. Application Data

[63] Continuation of Ser. No. 169,855, Jul. 17, 1980, abandoned.

[30] Foreign Application Priority Data

Jul. 20, 1979 [FR] France ................ 79 18780

[51] Int. Cl.$^4$ ............... A61K 31/745; A61K 31/715; A61K 31/725; C07H 5/06
[52] U.S. Cl. ........................ 424/83; 514/59; 514/56; 514/822; 536/21; 536/51; 525/330.7; 525/352; 525/374
[58] Field of Search ............ 514/56, 59; 536/51, 536/21; 424/83, 78, 79; 525/330.7, 352, 374, 366; 523/112

[56] References Cited

U.S. PATENT DOCUMENTS

| | | | |
|---|---|---|---|
| 3,211,617 | 10/1965 | Bucourt ................ | 536/21 |
| 3,475,358 | 10/1969 | Bixler et al. .......... | 523/112 |
| 3,697,498 | 10/1972 | Browning et al. ...... | 536/8 |
| 3,766,104 | 10/1973 | Bonin et al. .......... | 523/112 |
| 3,862,309 | 1/1975 | Krochock .............. | 424/78 |
| 3,893,890 | 7/1975 | Wurzburg .............. | 424/78 |
| 3,907,755 | 9/1975 | Margraff ............... | 424/78 |
| 3,961,045 | 6/1976 | Wurzburg et al. ...... | 424/78 |
| 3,987,163 | 10/1976 | Rankin ................. | 424/78 |
| 3,998,796 | 12/1976 | Sleinhardt ............. | 525/353 |
| 4,095,000 | 6/1978 | Brenner ................ | 514/56 |
| 4,116,898 | 9/1978 | Dudley et al. ......... | 523/112 |
| 4,119,616 | 10/1978 | O'Farrell et al. ..... | 525/353 |
| 4,271,151 | 6/1981 | Hoffa et al. ........... | 514/56 |
| 4,303,786 | 2/1981 | Goldstein et al. ..... | 536/51 |

FOREIGN PATENT DOCUMENTS

| | | |
|---|---|---|
| 2728718 | 11/1978 | Fed. Rep. of Germany . |
| 2066460 | 7/1971 | France . |
| 2078435 | 10/1971 | France . |

OTHER PUBLICATIONS

Vesa, Moroscikas, CA. 77 115177V (1972), Dissymmetric Ion-Exchange Resins Derived from amino Acids and Chlorosulfonated Styren-Divinyl Benzene Copolymers.
Chem. Abst., 77: 115,177u, 1972.

*Primary Examiner*—John Rollins
*Attorney, Agent, or Firm*—Weiser & Stapler

[57] ABSTRACT

Anticoagulant products are constituted by polymers (homopolymers or copolymers) including in their chain substitutable groups on which are fixed statistically, groups X and/or Y and/or V, where X denotes the group —$SO_3R_1$ or —$R_3$—$SO_3R_1$, $R_1$ being a hydrogen atom or a physiologically compatible metal, $R_3$ being a —$CH_2$—CO—NH—$R_4$ group in which $R_4$ represensts an alkyl aryl or alkylaryl radical, which may or may not be substituted, or substituted or unsubstituted —$CH_2$—; Y denotes the group —$SO_2$ —$R_2$ or —$R_3$ —$SO_2$—$R_2$, $R_2$ being the residue of an amino acid connected to the —$SO_2$ bridge through its amine function and V denotes the group —$CH_2$—CO—NH—CHR—COOH, R being the side chain of an amino acid it being understood that: (a) if X is —$SO_3 R_1$ it is necessarily accompanied by Y and/or by V, and (b) V is always accompanied by X and/by Y.

30 Claims, 5 Drawing Sheets

POLYMERS SUBSTITUTED BY GROUPS CONFERRING ANTI-COAGULANT PROPERTIES ON THEM, PROCESS FOR THEIR PREPARATION, ARTICLES AND COMPOSITIONS MADE THEREFROM AND USES THEREOF

This application is a continuation of application Ser. No. 169,855, filed July 17, 1980, now abandoned.

BACKGROUND OF THE INVENTION

1. Field of the Invention

The present invention relates to polymers substituted by groups conferring anticoagulant properties on them, to the process for their preparation, to articles constituted by and/or comprising said substituted polymers, the processes for their manufacture and to the uses of said articles in surgery and in medicine, and pharmaceutical compositions containing said substituted polymers.

2. Description of the Prior Art

Heparin, the natural anticoagulant agent of the blood, constitutes a medicament of choice in thromboembolic disorders. consequently, in order to overcome the drawbacks of heparin, for a certain number of years already, attempts have been made to provide a substitute for this valuable material by various synthetic or semi-synthetic products.

In this role there have been recognized: -chondroitin sulfate, (which is also a heterogeneous polyholoside), chitosan (a scission product of chitin) prepared by the complete N-deacetylation of chitin (HORTON and JUST "carbohydrate Research" 29 (1973) 173–179), sulfated chitosan (WOLFROM and SHENHAN, JACS (1959) 81, 1764–1766), heparan sulfate (JORPES and GARDELL "J. Biol. Chem." 176–267 (1948)) and other polysaccharides formed by the polymerisation of a disaccharide unit constituted by an osamine (principally D-glucosamine) bearing a certain number of sulfate and/or sulfonate groups and by a uronic acid (generally D-glucuronic acid and L-iduronic acid). Apart from the fact that the "heparin-like" action of these various products is less pronounced than that of heparin, their natural origin is the cause (as is the case for heparin) of their variability and their heterogeneity from one preparation to the next.

Another series of heparinoids is constituted by products derived from amylose (which, like heparin has (1 4) bonds, which have been studied, among others, by WOLFROM and WANG (Carbohydrate Research 18 (1971) 23–27) relating to aminated and sulfated amylose and by HORTON and JUST (Carbohydrate Research 30 (1973) 349–357) relating to conversion of amylose into (1→4) 2-amino-2-deoxy-αD-glucopyranuronane. The products so obtained have a weak or practically zero heparinic activity (aminated and sulfated amylose).

Certain other polysaccharides have been indicated for their more or less anticoagulant properties: dextran sulfate (V. POTUZNIK J. Hyg. Epid. Microbiol. Immunol. 16, 293 (1972)); sulfuric polyester of pentosan (a product sold under the name "HEMOCLAR" by CLIN-MIDY Laboratories); or derivatives of alginic acid (L. LARM and collab. Carbohydr. Res. 73, 332 (1979)). Unfortunately, none of these products can be validly compared with heparin.

Sulfonated derivatives of polypeptides, namely copolymers of lysin and of tryptophane, have also been proposed (French Pat. No. 2, 280, 387). If these products in fact cause a very distinct prolongation of the coagulation time and have an action of the same type as that of heparin, they cannot be used on a large scale, since the side reactions that they cause in the human organism are extremely troublesome.

In 1975, Harry P. GREGOR (Polym. Sci. Technol. U.S.A. (1975) 7, 51–56) recognized the use, as "heparin-like" materials, of sulfonated polymers and copolymers (in particular polystyrenesulfonic and polyethylenesulfonic acids). T. BEUGELING and Collab. (J. BIOMED. MATER. RES. (1974) Vol. 8, 375–379 and BIOCOMPAT. IMPLANT. MATER, 187192 (1976)) recognized the use of polymers synthesized from polyisoprenes, of which the unit is represented as follows:

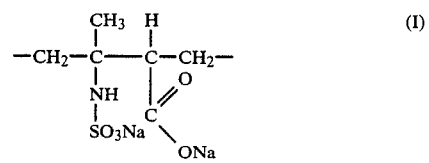

which are derivatives containing aminosulfonate and carboxylate groups.

These Authors have obtained essentially soluble derivatives whose anticoagulant activity only represents however 12 to 15% of that of heparin taken as a reference.

Other interesting attempts have been carried out by grafting the heparin molecule itself on to the surface of polymers (for example by means of a coupling agent constituted by tridodecylmethylammonium chloride: LEININGER and Collab. in Trans. Amer. Soc. Artif. Int. Organs 18 10 (1972), etc . . . ) or by a covalent bond: (HOFFMAN and Collab. in Trans. Amer. Soc. Artif. Int. Organs. 18 10 (1972), ect . . . ). Unfortunately, apart from the fact that the fixing of only a relatively small amount of heparin has been acheived, these "heparinized" polymers are not stable: the amount fixed has a tendency to become inactivated with time.

In general, the advantage which would exist in having available a product with anticoagulant action which is not only stable, reproducible and homogeneous from one batch to the next, but also insoluble if desired, is the stimulus of numerous research studies for new anticoagulants.

Thus very active products have been obtained by chemical or radiochemical grafting or vinyl monomers on heparin (compare the work of C. BAQUEY and Collab. in Ann. Phys. Biol. Med. 9(2) 131–138 (1975) and of D. LABARRE, Thèse de Doctorat d'Etat Paris (1977)). The insoluble polymers thus obtained are unusable in practice, since in addition to the inactivation that they undergo with time, the grafted heparin migrates to the inside of the molecule in the couse of the application of these products, and becomes completely masked.

On examining the anticoagulant properties of the various compounds enumerated above, Applicants have formulated a hypothesis according to which the anticoagulant properties of heparin are not bound up with its secondary or tertiary structure, but more precisely with the nature of the various groups borne by the polysaccharide chain and with the combination of effects of these groups, which would have a cooperative result multiplying the activity of each of them relative to the thrombin and antithrombin III.

It is considered that heparin, generally represented by the formula II below:

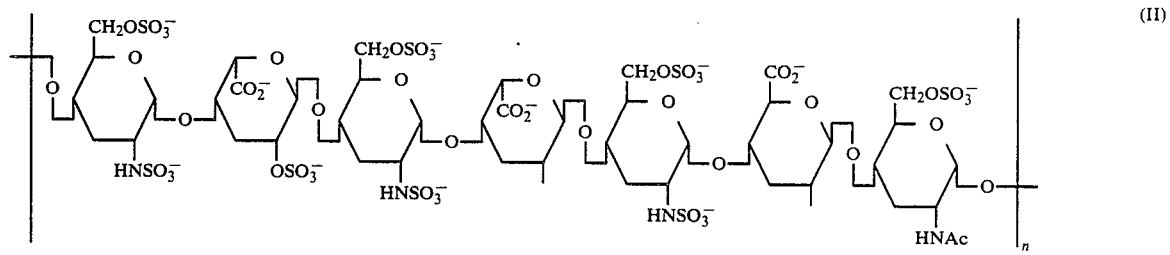

possesses also non O-sulfated or 2-O-sulfated units of the uronic residue

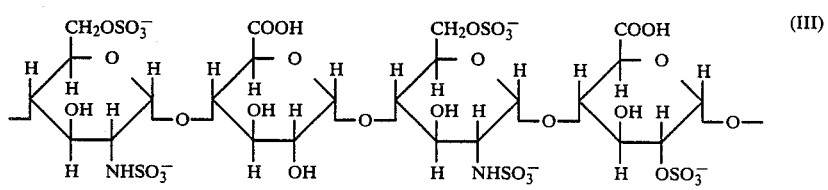

In addition, ion exchange resins useful for the liquid chromatography of recemic mixtures have been prepared, which resins are essentially constituted by polystyrenes on which the following amino acids have been fixed: alanine, valine, norvaline, phenylalanine, leucine, isoleucine, tyrosine, serine, threonine, aspartic acid, proline, hydroxyproline and glutamic acid (compare in particular the studies carried out by VESA and Collab., Zh. Obsch. Khim. SSSR 42 (12) 2780 (1972) and Tr. Akad. Nauk. Lit. SSR. Ser. B. 2-69, 93 (1972) and by PETIT and JOZEFONVICZ (Jour, Of Applied Polymer Sci. Vol. 21 2589-2596 (1977)).

Starting from their hypothesis relative to the importance of the simultaneous presence of groups which figure in the above formulae II and III, on a macromolecular support, Applicants have been able to establish that such ion exchange resins have applications as agents endowed with anticoagulant action.

Better still, through their comprehension of this phenomenon and pressing their studies and their investigations still further, Applicants have been able to establish a more general formula suitable for all polymers crosslinked or not and including in their chain substitutable groups. They have been able to arrive in this way at both soluble and insoluble products, having anticoagulant properties.

GENERAL DESCRIPTION OF THE INVENTION

According to the present invention products endowed with anticoagulant properties are provided, said products being characterised in that they are constituted by polymers (homopolymers or copolymers) including in their chain substitutable groups on which are fixed statistically, groups X and/or Y and/or V, where X denotes the $-SO_3R_1$ or $-R_3-SO_3R_1$ group $R_1$ being a hydrogen atom or a physiologically compatible metal, $R_3$ being a $-CH_2-CO-NH-R_4$ group $R_4$ represents an alkyl, aryl or alkylaryl radical, substituted or not or substituted or not Y denotes the group $-SO_2R_2$ or $R_3-SO_2-R_2$ $R_2$ being the residue of an amino acid joined to the $-SO_2-$ bridge by its amine function and V denotes the group $-CH_2-CO-NH-CHR-COOH$ R being the side chain of an amino acid, it being well understood that:

(a) if X is $-SO_3R_1$ it is necessarily accompanied by Y and/or by V, and (b) V is always accompanied by X and/or by Y.

In accordance with the invention, the amino acids are selected from among those which include at least one free carboxylic function and if they possess other amine functions, all except one must be blocked by a physiologically acceptable electroattractor group.

According to a particular modification of this embodiment, the electroattractor group is advantageously constituted by the benzyloxycarbonyl or tertiobutyloxycarbonyl group.

In accordance with the invention, the amino acids are selected from the group which comprises glutamic acid, aspartic acid, methionine, cysteine, cysteic acid, proline, hydroxyproline, threonine, serine, tyrosine, alanine, phenylalanine, valine, leucine, benzyloxycarbonyl-lysine, tertiobutyloxycarbonyl-lysine, ε-aminocaproic acid, β-alanine, γ-amino-n-butyric acid, δ-amino-n-valeric acid, which may be substituted or not.

According to an advantageous embodiment of the present invention, the polymers bearing fixed X, and/or Y and/or V groups, are crosslinked polymers.

The products thus obtained, which are insoluble in water and in biological fluids, enable various articles to be fashioned such as cardiovascular prostheses, catheters, suturing threads, etc . . . , of anticoagulant material.

According to another advantageous embodiment of the present invention, the polymers bearing X, and/or Y, and/or V groups fixed to their macromolecular chains, are noncrosslinked and soluble polymers.

The products thus obtained which are soluble in water and in biological fluids enable the preparation of solutions with anticoagulant action for pharmaceutical use.

According to an advantageous embodiment of the present invention, the polymers, crosslinked or not, including in their chain substitutable groups on which are fixed the groups X and/or Y and/or V, are polystyrenes.

According to another advantageous embodiment of the invention, the crosslinked or uncrosslinked polymers, including in their chain substitutable groups on which are fixed the X and/or Y and/or V groups are polysaccharides.

According to a particular modification of this embodiment, the polymers are constituted by dextrans. The biocompatibility of the dextrans with blood has long been known. A. GRONWALL and Collab. (Acta. Physiol. Scand. 7 97 (1944)) recognized their usefulness as a blood plasma substitute and W. APPEL and Collab. (Angew. Chem. Intern. Ed. 7, 702 (1968)) studied their enzymatic degradation in the plasma and the tissues under the action of dextranase.

According to another aspect of the present invention there is provided a process for the preparation of products endowed with anticoagulant activity in accordance with the present invention which process, in the case where it is desired to obtain products in which:
X=—$SO_3R_1$
Y=—$SO_2$—$R_2$
and V is nil
($R_1$ and $R_2$ having the same meaning as above),
is characterised in that in the course of a first step, a chlorosulfonated polymer POL—$SO_2Cl$ is prepared by the reaction of chlorosulfonic acid on the polymer in a suitable solvent and in that in the course of a second step the —$SO_2Cl$ groups are converted into —$SO_3Na$ groups and into $SO_2AA$ groups (where AA represents an amino acid) by reaction with a suitable amount of an amino acid in a basic medium.

According to a particular modification of this embodiment in the case where it is desired to obtain soluble substituted polymers with anticoagulant action, the sulfonation of the uncrosslinked polymer takes place in an organic medium advantageously constituted by a chlorinated solvent and more particularly by dichloromethane, the polymer is precipitated in nitromethane and the reaction with the amino acid takes place in a medium containing the mixture water-dioxane.

According to a particular modification of this embodiment, in the case where it is desired to obtain insoluble substituted polymers with anticoagulant action, the sulfonation of the crosslinked polymer takes place in a mixture containing dichloromethane and nitromethane, and the reaction with the amino acid takes place in a medium containing the water-dioxane mixture.

According to a particular modification of this embodiment and in order to remove as completely as possible any impurity capable of interacting with the coagulation factors, there follows in the case of insoluble polymers, after the fixing of the amino acids, an abundant washing with water followed by washings by a solution of NaCl (1.5M), then washings with Na citrate (1M), by equilibrating at pH about 7.30 by several washings with MICHAELIS buffer, another washing with water and finally drying.

According to a particular modification of this embodiment, in the case of soluble polymers, the impurities are removed after the fixing of the amino acid by dialysis against water and there is recovered, if desired, the pure finished product by freeze-drying.

According to the invention, in the case where it is desired to obtain the products in which
X=—$R_3$—$SO_3R_1$
V=—$CH_2$—CO—NH—CHR—COOH
and Y is nil
($R_1$ and $R_3$ having the same significance as above), the process is characterised in that there is prepared in the course of a first step the carboxymethylated derivatives of the polymers, in that in the course of a second step suitable amines or benzyl chloride are fixed, in that the amino acids are fixed in the course of the third step and in that the sulfonation proceeds in the course of a fourth step.

According to a particular modification of this embodiment, the coupling of the amines and/or of the amino acids on the carboxymethylated derivatives of the polymers, is carried out by means of N-ethoxycarbonyl-2-ethoxy 1,2-dihydroquinoline or other similar coupling agents.

According to a particular modification of this embodiment, the sulfonation step is repeated several times if it is desired to increase the proportion of sulfonate groups.

According to another particular modification of this embodiment, in the case of soluble, uncrosslinked polymers, the final product is purified by ultrafiltration under pressure.

In accordance with the invention, in the case where it is desired to obtain products in which:
X=—$R_3$—$SO_3R_1$
V=—$CH_2$—CO—NH—CHR—COOH
and Y=—$R_3$—$SO_2$—$R_1$
R, $R_1$, $R_2$ and $R_3$ having the same meaning as above, the process is characterised in that in the course of a first step, carboxymethylation proceeds, and that in the course of a second step suitable amines are or benzyl chloride are fixed, and that in the course of a third step chlorosulfonation follows, and that in the course of the fourth step the amino acids are fixed.

According to another aspect of the present invention there are provided articles for medical and surgical use such as tubes, cardiovascular prostheses, catheters, threads, films and the like on polymers including substitutable groups, rendered anticoagulant by fixing to their outer surface X, and/or Y, and/or V groups such as previously defined. In other words, it suffices firstly to fashion an article of form and dimensions desired from a polymer including substitutable groups, then of fixing chemically (by putting into use, for example, the process described above) the X, and/or Y, and/or V groups in the desired amounts and as high as desired, to obtain a solid material with anticoagulant action, very stable in time, and not undergoing any salting-out nor degradation.

According to another aspect of the present invention pharmaceutical compositions are provided constituted by, or containing uncrosslinked polymers substituted by groups conferring on them anticoagulant activity and soluble in water, said polymers being present in said pharmaceutical compositions in the proportion of a therapeutically active dose.

Apart from the foregoing features, the invention comprises still other features which will emerge from the description which follows.

The present invention relates more particularly to the use of polymers including X, and/or Y, and/or V groups as defined above, fixed to their macromolecular chain, as products with an action similar to that of heparin, as well as articles manufactured from these polymers.

DESCRIPTION OF PREFERRED EMBODIMENTS

Figure 1A:
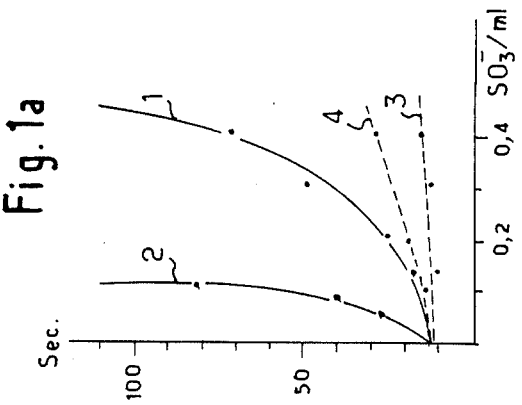

The invention will be better understood on reading the further description which follows, which refers to examples of the preparation and of the characterisation of products according to the present invention, to a study of the anticoagulant activity, and other properties analogous to those of heparin of these products, and to an evaluation of the activity itself of each type of substituent.

It must be well understood, however, that the various examples, characteristics and studies which are described below and illustrated in the accompanying drawings, are given purely by way of illustration of the invention, but constitute in no way a limitation thereof.

I—PREPARATION OF MATERIALS AND REACTANTS IN WHICH POLYSTYRENE (PS) IS THE SUPPORTING POLYMER

The following materials were prepared:

(a) Products with anticoagulant activity according to the invention

| reference number | name of the product |
| --- | --- |
| 1 | PS—hydroxyproline |
| 2 | PS—proline |
| 3 | PS—alanine |
| 4 | PS—phenylalanine |
| 5 | PS—glutamic acid |
| 6 | PS—methionine |
| 7 | PS—threonine |
| 8 | PS—$\alpha$ or $\epsilon$-benzyloxycarbonyl-lysine |
| 9 | PS—$\epsilon$-tertiobutyloxycarbonyllysine |
| 16 | PS—aspartic acid |
| 17 | PS—$\beta$alanine |
| 18 | PS—$\epsilon$-aminocaproic acid |
| (b) Study and comparison products | |
| 10 | PS—lysine (diamino-acid) |
| 11 | PS—$CH_2$—Proline (the amino acid is fixed through the —$CH_2$— bridge) |
| 12 | PS—$CH_2$—hydroxyproline (the amino acid is fixed through the —$CH_2$— bridge) |
| 13 | PS—$CH_2$—alanine (the amino acid is fixed through the —$CH_2$—bridge) |
| 14 | PS—butylamine (fixing of an amine and no longer of an amino acid |
| 15 | PS—$SO_3$ (resin sulfonated only) |

The starting polystyrene is a copolymer of styrene and 2% of divinylbenzene, marketed by FLUKA. It is used in the form of beads of 200 to 400 diameters mesh, mainly between 0.037 and 0.074 mm diameter. The commercial product is washed successively with a 1M solution of NaOH, with water, a 1M solution of HCl and of water. It is dried under vacuum at 60° C.

The amino acids used are "FLUKA Puriss" reactants.

(c) Preparation of PS—$SO_3$ (15)

25 g of polystyrene in 200 ml of dichloromethane is left to swell overnight, at ambient temperature. Then a mixture of 160 ml of nitromethane and 140 ml of chlorosulfonic acid is added. The suspension is shaken for 7 hours at 40° C. The crude resin is then filtered, washed carefully with nitromethane and with acetone. It is finally dried under vacuum at 50° C.

The proportion of chlorosulfonyl groups (—$SO_2Cl$) is determined as follows: 200 mg of chlorosulfonated polystyrene were hydrolysed with 50 ml of 1M solution of NaOH for 24 hours under reflux. After acidification, the $Cl^-$ ions were titrated with a 0.1M solution of $AgNO_3$, using a silver indicator electrode.

The sulfonated polystyrene was quantitatively hydrolysed with 2M soda at ambiant temperature. It was filtered, washed with water and dried under vacuum.

(d) Preparation of products 1, 2, 3, 4, 5, 6, 7, 8, 9, 10, 14, 16, 17, 18

86 mmoles of amino acid were dissolved in 130 ml of a 3:2 water-dioxane mixture by the addition of the minimum of 4M soda. The pH was then measured and then 10 g of chlorosulfonated polystyrene was added as obtained above (43 meq —$SO_2Cl$). The pH was then kept at its initial value by the addition of 2M soda. The reaction was stopped when the pH remained stable. The polymer was then filtered, washed abondantly with water, with $10^{-2}M$ soda and with water. It was finally dried under vacuum.

(e) Preparation of a polystyrene resin containing only amino acid —$SO_2$ groups and not sulfonate groups (—$SO_3R_1$)

86 mmoles of the methyl ester of the amino acid were dissolved in 250 ml of dichloromethane. Then 10 g of the chlorosulfonated polystyrene as obtained above were added. The mixture was stirred for 48 hours at 40° C. The polymer was then filtered, washed abondantly with ethanol and then dried under vacuum. The hydrolysis of the methyl ester was carried out in 2M of soda and led to the resin containing exclusively amino acid sulfamide groups whose carboxylic functions are free.

(f) Preparation of PS—$CH_2$—AA polymers 11, 12, 13 (the amino acid is fixed to the polystyrene through the —$CH_2$— bridge)

First step: Preparation of chloromethylated polystyrene 25 g of crosslinked polystyrene was allowed to swell for 30 min at 25° C. in 150 ml of chloroform. Then 100 ml of monochlorodimethyl ether and 10 ml of stannic chloride was added. The reaction was allowed to continue for 1.5 hours with stirring at ambient temperature. The resin was then filtered, washed with a 3/1 mixture of dioxane/water, then with a 3/1 mixture of dioxane/3N hydrochloric acid. The polymer was then washed with water/dioxane mixtures richer and richer in dioxane, with dioxane, and then with mixtures of dioxane/methanol richer and richer in methanol, and finally with methanol. The resin was then dried under vacuum at 50° C.

The proportion of chloromethyl groups (—$CH_2Cl$) was determined in the following manner: 200 mg of chloromethylated polystrene were quaternized in 5 ml of pure butylamine at boiling point for 6 hours. After acidification of the medium with nitric acid, the $Cl^-$ ions were titrated with an 0.1M solution of $AgNO_3$ using a silver indicator electrode.

Second step: production of the sulfonium salt 20 g of chloromethylated polystyrene (80 mmoles) were suspended in a mixture of 30 ml of dimethylsulfide (400 mmoles), 100 ml of water and 120 ml of isopropanol. The mixture was stirred for 48 hours at ambiant temperature. The yield of the reaction was determined by potentiometric titration of the $Cl^-$ ions contained in an aliquot part of the reaction medium. The yield was about 80%. The sulfonium salt was not isolated.

Third step: fixing of the amino acid

To the preceding suspension, 64 mmoles of soda and 120 mmoles of the sodium salt of the amino acid in 170 ml of isopropanol and 200 ml of water (ratioAA/—$CH_2S^+(CH_3)_2$ groups=2) were added. The reaction mixture was stirred under reflux for 24 hours. The crude resin was then filtered and resuspended in 4M ammonia under reflux for 4 hours, to remove the dimethylsulfide. The PS—$CH_2$—AA polymer was then filtered, washed successively with water, with 1M HCl, with water and with 1M soda. It was then washed several times with water until the filtrate was neutral. The polymer was then dried under vacuum.

The characteristics of the products prepared according to (d) and (f) are summarized in Table I below.

TABLE I

| Fixed amino acid | Ratio AA AA/$SO_2Cl$ | AA (meq/g) | $SO_3^-$ (meq/g) | ACTIVITY (meq$^{-1}$) |
|---|---|---|---|---|
| 1 | 1.6 | 2.23 | 0.93 | 91 |
|   | 0.6 | 1.90 | 1.37 | 126 |
|   | 0.4 | 1.37 | 2.16 | 179 |
|   | 0.2 | 0.67 | 3.17 | 43 |
| 2 | 2 | 2.59 | 0.48 | 119 |
|   | 1.5 | 2.08 | 1.14 | 91 |
|   | 1 | 2.10 | 1.05 | 86 |
|   | 0.6 | 1.63 | 1.83 | 78 |
|   | 0.3 | 0.93 | 2.99 | 50 |
| 3 | 2 | 2.78 | 0.67 | 70 |
|   | 1.5 | 2.58 | 0.90 | 106 |
|   | 1 | 2.20 | 1.24 | 57 |
|   | 0.3 | 0.81 | 3.08 | 48 |
| 4 | 2 | 2.21 | 0.79 | 59 |
|   | 1.5 | 2.14 | 0.79 | 60 |
|   | 1 | 2.03 | 1.15 | 50 |
|   | 0.6 | 1.51 | 1.73 | 47 |
|   | 0.3 | 0.90 | 2.92 | 42 |
| 5 | 2 | 1.33 | 2.02 | 214 |
|   | 1.2 | 1.5 | 1.80 | 136 |
|   | 1.6 | 1.0 | 2.32 | 89 |
|   | 0.8 | 0.82 | 2.63 | 71 |
|   | 0.7 | 0.31 | 3.43 | 84 |
| 6 | 2 | 2.34 | 0.43 | 119 |
|   | 1.8 | 2.28 | 0.49 | 83 |
|   | 1.3 | 1.89 | 0.94 | 100 |
|   | 1 | 1.69 | 1.37 | 77 |
|   | 0.8 | 1.45 | 1.90 | 62 |
|   | 0.7 | 1.24 | 2.14 | 68 |
| 7 | 2 | 2.41 | 0.93 | 120 |
|   | 1.6 | 2.38 | 1.01 | 127 |
|   | 1.2 | 2.22 | 1.21 | 107 |
|   | 0.8 | 2.02 | 1.53 | 95 |
|   | 0.6 | 1.58 | 1.97 | 52 |
|   | 0.3 | 0.79 | 2.86 | 55 |
| 8 | 1 | 1.41 | 1.20 | 75 |
|   | 2 | 1.34 | 1.34 | 58 |
|   | 0.6 | 1.11 | 1.87 | 65 |
|   | 0.3 | 0.75 | 2.59 | 63 |
| 9 | 1 | 0.95 | 2.30 | 58 |
|   | 0.6 | 0.88 | 2.53 | 52 |
|   | 1 | 0.75 | 2.64 | 49 |
|   | 2 | 1.03 | 2.22 | 99 |
| 10 | 1 | 1.56 | 1.94 | 36 |
| 11 | 2 | 1.2 | — | — |
| 12 | 2 | 1.0 | — | — |
| 13 | 1.4 | 0.8 | — | — |
| 14 | 1 | 3.14 | 0.88 | 11 |
|    | 0.6 | 2.08 | 1.94 | 22 |
|    | 0.5 | 1.77 | 2.21 | 50 |
|    | 0.3 | 1.09 | 3.01 | 45 |

(g) Preparation of soluble products with anticoagulant action

First step: synthesis of chlorosulfonated polystyrene 25 g of uncrosslinked polystyrene were dissolved in 200 ml of dichloromethane. Then with vigorous stirring, 16 ml of chlorosulfonic acid was added and the reaction was allowed to continue for 7 hours at 40° C. Nitromethane was then added to precipitate all the polymer. It was filtered and washed with nitromethane to remove every trace of chlorosulfonic acid. The polymer was then dried under vacuum. The proportion of chlorosulfonyl groups was determined in the following manner: 200 mg of chlorosulfonated polystyrene were hydrolysed with 50 ml of 1M solution of NaOH for 24 hours uder reflux. After acidification, the $Cl^-$ ions were titrated with an 0.1M solution of $AgNO_3$ using a silver indicator electrode.

Second step: fixing of the amino acid 50 mmoles of amino acid (in the form of a sodium salt) were dissolved in 100 ml of 3-2 water-dioxane mixture. The pH was measured and 10 g of the preceding polymer added. The pH was then kept at its initial value as measured, by the addition of 2M of soda. The reaction was stopped when the pH remained stable. The reaction medium was then dialysed against water and the pure product recovered by lyophilisation.

(h) Conditioning and granulometry

The starting polystyrene was a commercial resin whose spherical grains had an average diameter of 30 to 80μ. The fixing of the various functions modifies the size of the grains little in the dry state, but substantially increases their dimensions in suspension in an aqueous medium, since these functions give the thus modified polystyrene a marked hydrophilic character.

A preliminary study having shown that the anticoagulant activity is a function of the specific surface of the grains, the latter was increased by grinding. The ground samples were then suspended in MICHAELIS buffer and fractionnated according to the size of the grains, in order to remove the particles of an average diameter less than about 2μ which remain in quasi-colloidal suspension.

Thus, the beads of different crude polymers obtained, were first washed, equilibrated to pH 7.35 (MICHAELIS buffer), then dried. The resin beads were then ground (by very rapid movements of agate balls in an agate mold), in order to reduce the size of the particles studied. To remove the very fine particles, the crude product was washed several times by suspension in MICHAELIS buffer, followed by a decantation and removal of the supernatant liquor. The particle size distribution of the specimens obtained was determined by quantitative microscopy ("Technic Analysis System"). This fractionation as a function of the size of the particles, makes possible the study of the anticoagulant activity on samples whose distribution of grain dimensions is almost identical.

II—PREPARATION OF MATERIALS HAVING DEXTRAN AS A SUPPORT POLYMER

A—Synthesis of unsoluble, uncrosslinked compounds (a) Preparation of:

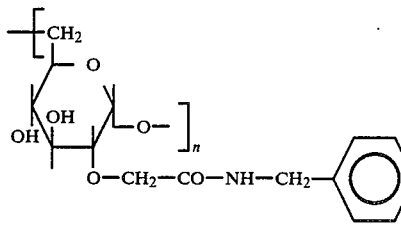 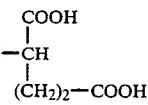

First step: Carboxymethylation of dextrans (Procedure was taken from the work of E. Antonini and Collab. (Giorn. Biochi. 14 88 (1965))).

In a flask of 1 l with a flat bottom provided with a stirring system, immersed to ⅔ in an oil bath, and surmounted by a condenser, was dissolved at ambient temperature 16.2 g of dextran (0.1 mole) in 500 ml of 12M soda (6 moles). It was taken to a temperature close to 70° C. and kept at that temperature for 3 hours. Then little by little 283.5 g of ClCH₂COOH (3 moles) were introduced into this mixture still kept at about 70° C.; the time of addition was about one half hour). It was left under stirring (still at about 70° C.) for 24 hours. It was then allowed to come back to ambiant temperature, then precipitated in 1.5 liter of methanol, the precipitated product was then separated by filtration, it was washed with a little methanol, then redissolved in about 100 ml of distilled water. It was again precipitated in about 500 ml of methanol, filtered, washed and dried in an oven under vacuum at about 40° C.

Second step: Fixing of benzylamine

In a flat bottom flask of 200 ml, provided with a stirring system, was dissolved, at ambiant temperature, 5 g of carboxymethyl-dextran (prepared in the course of the previous step) in 20 ml of distilled water. The pH of the medium was adjusted to about 4 with a little concentrated hydrochloric acid. Then slowly (duration of addition: 15 minutes approximately) 6 g of EEDQ dissolved in 50 ml of absolute ethanol was poured in. The stirring was kept up for one half hour and then 3 ml of benzylamine added and it was left under stirring over night. The mixture was then poured into 700 ml of

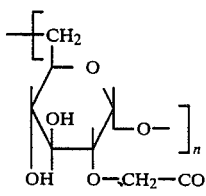

acetone, the precipitate formed was filtered, washed with acetone and dried in the oven under vacuum.

Third step: Fixing of the glutamic acid 2 g of the product prepared in the course of the second step was dissolved in 10 ml of distilled water and the pH was adjusted to 4 by some drops of concentrated HCl. Slowly 1.7 g of EEDQ dissolved in 13 ml was then added too. It was left with stirring for a half hour and then to this reaction mixture was added 10 ml of a aqueous solution containing 1.6 g of glutamic acid and 0.87 g of soda. It was left with stirring overnight at ambiant temperature. The mixture was then acidified (pH comprised between 4 and 5) by means of HCl, then precipitated in 800 ml of methanol. The precipitated product was then separated by filtration, washed with methanol, then dried in the oven under vacuum overnight.

Fourth step: Sulfonation 1.2 g of the product obtained in the course of the the third step was weighed and it was placed—with stirring—in 100 ml of nitromethane. Then slowly 1.4 ml of chlorosulfonic acid was added and it was left with stirring for 2 hours. The product formed was separated by filtration, washed with nitromethane, the product placed for 2 hours in M soda, precipitated with methanol, washed and dried under vacuum.

Fifth step: Purification

The dry product obtained in the course of the fourth step was treated in an ultrafiltration cell (5000 membrane) in the presence of double-distilled water, under a pressure of 2 bars, for 3 days.

(b) Preparation of:

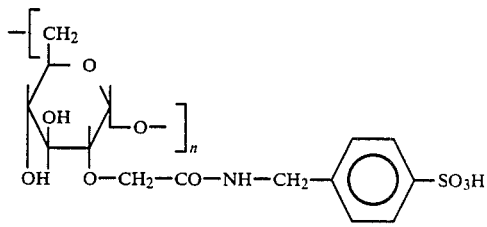

In order, the steps (1), (2), (4) and (5) of Example III (a) were carried out.

B—Synthesis of insoluble crosslinked compounds

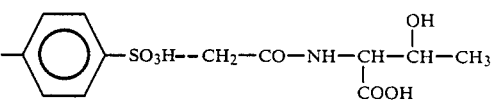

Starting material:

Carboxymethyl-Sephadex (4.0–4.5 meq/g) placed in the acid form.

(1) Fixing of benzylamine in a 250 cm³ flask, was dispersed with stirring 5 g of carboxymethyl-Sephadex in 60 cm³ of water;

slowly a solution of 20 g of EEDQ dissolved in 160 ml of absolute ethanol was added and it was allowed to act for one half hour;

4.4 cm³ of benzylamine were added;

the mixture was allowed to stand with stirring for 24 hours;

it was filtered to recover the product;

it was washed abundantly with distilled water, then with absolute ethanol and once more with water;

it was dried in the oven under vacuum at 40° C. for 24 hours, about 2 to 2.6 meq/g of benzylamine was fixed.

(2) Fixing of threonine

In a 250 cm³ flask, 6 g of the preceding product were dispersed in 60 cm³ of distilled water.

slowly a solution of 20 g of EEDQ dissolved in 160 ml of absolute ethanol was added and it was allowed to act for one half hour;

then the following mixture was added:

3 g of threonine 1.1 g of soda 20 cm³ of distilled water and it was left with stirring for 24 hours;

then the product was recovered as described at (1); about 1.6 meq/g of threonine was fixed.

(3) Sulfonation 5 g of the preceding product were dispersed in 500 cm³ of nitromethane with stirring;

slowly 2.8 cm³ of chlorosulfonic acid (amount corresponding to about 3 times the amount of benzylamine); was added was left to act for 2 hours;

the product was recovered by filtration;

it was washed abundantly with nitromethane then with distilled water;

the product obtained was placed in a solution of 1M of soda for 2 hours in order to completely hydrolyse it;

the product was recovered by filtration;

it was washed abundantly with distilled water, and dried in the oven under vacuum at 40° C. for 24 hours.

If working in the presence of a larger excess of chlorosulfonic acid (>4 times the amount of benzylamine), a soluble product is obtained.

(4) Washing and conditioning of the product

In order to remove completely the synthesis reactants, the product is subjected successively to two washings with a 1.5M of sodium chloride solution, then two washings with a molar solution of trisodium citrate.

It is then conditioned at pH 7.3-7.35 by three successive washings with MICHAELIS buffer.

The product is finally washed thoroughly with distilled water and dried in the oven under vacuum at 40° C. for 24 hours.

III—COAGULATION TESTS

The platelet impoverished plasma (PPP) is prepared from fresh human plasma by centrifugation (4° C.-10 000 g-30 minutes). It is stored at −20° C., defrosted in small amounts and then kept at 4° C.

The fibrinogen used is purified bovine fibrinogen (Behring) at a concentration of 6 g/l in 0.85% NaCl. The solution was made up just before use and preserved at 37° C.

The thrombin (Roche 50 NIH/mg), the heparin antagonist (polybene or polylysine (Sigma)) were diluted extemporaneouly in MICHAELIS buffer and preserved at 4° C. (for the thrombin) or at room temperature (for the polybrene and the polylysine). The reptilase (Stago) was diluted in distilled water and preserved at 37° C. The antithrombin III (Kabi) was in solution in distilled water and preserved at 4° C.

The polymers were in suspension in MICHAELIS buffer supplemented with 1 g/l of an emulsifying agent (Lensex TA 01—NP 40 Shell).

All the coagulation times were determined at 37° C. in a glass tube by direct observation.

IV—STUDY OF ANTICOAGULANT ACTIVITY

The anticoagulant activity of the resins was studied by determination of the decalcified and platelet impoverished (PPP) plasma thrombin times or of the fibronogen solution in the presence of the resin to be studied in variable concentration. Preliminary studies of several resins PS-SO₃ containing varied proportions of —SO₃Na groups, have shown that the thrombin time only depends on the amount of —SO₃Na groups present in a given volume of PPP at the moment of test. Consequently, to be able to compare directly anticoagulant activity of different resins directly, the thrombin times were plotted as a function of the amount of resin expressed in concentration of —SO₃Na.

Figure 1B:
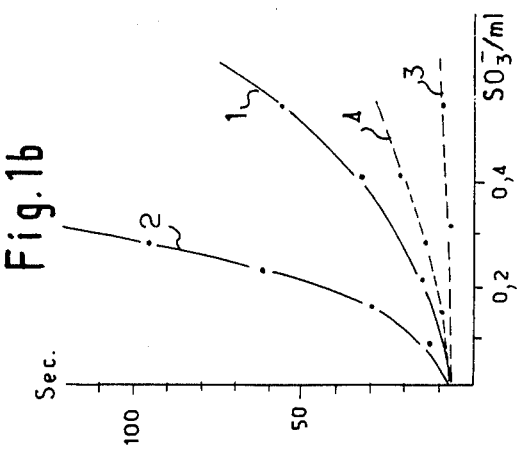
Figure 1C:
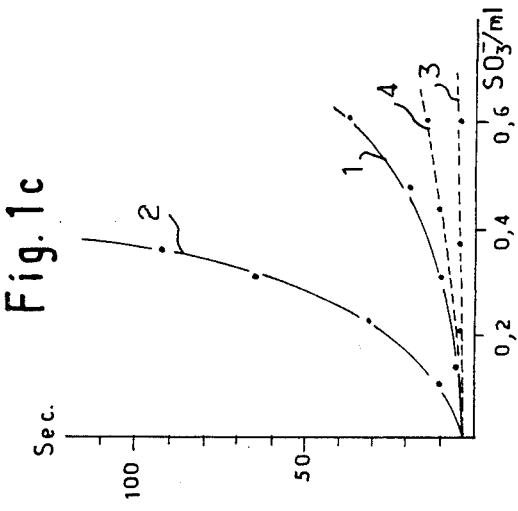

The results are shown in FIG. 1. The thrombin time in seconds is plotted as as ordinate, and the concentration of the polymer suspension (expressed in number of $SO_3^-$/ml) as abscissa for 30 U/ml of thrombin (FIG. 1a), 50 U/ml of thrombin (FIG. 1b) and 75 U/ml of thrombin (FIG. 1c)

The curves 1 correspond to the resin PS—SO₃ with PPP.

The curves 2 correspond to the resin PS—SO₂ with PPP.

The curves 3 correspond to the PS—SO₃ with the fibrinogen solution.

The curves 4 correspond to the resin PS—SO₂—Glu with the fibrinogen solution.

A suspension of 0.1 ml of polymer (of variable concentration) was incubated with 0.2 ml of PPP (continuous curves in FIG. 1) or of a fibrinogen solution (curves in dashed lines FIG. 1) for 30 minutes at 37° C. Then 0.1 ml of thrombin was added and the coagulation time measured.

On examining FIG. 1, it is immediately observed that the anticoagulant effect of the resin PS—SO₂—Glu is greater than that of the resin PS—SO₃. This difference cannot be attributed to the difference in the size of the grains or of specific surface, the latter being much too small to explain the deviations observed in the coagulation times.

In all cases, the following additional checks were performed:

(a) determination of the thrombin time of the PPP or of the fibrinogen solution in the absence of polymer (control times)

Figure 2:
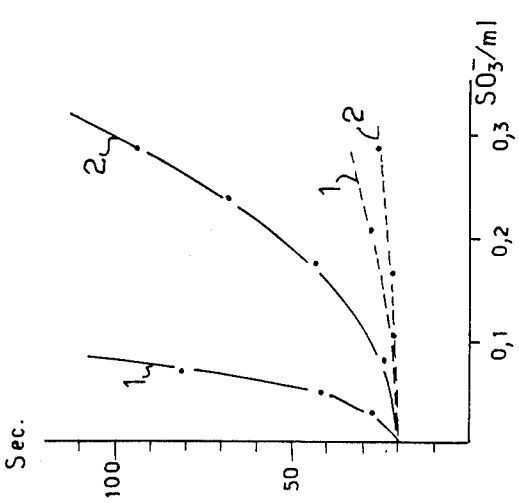

(b) determination of the thrombin time on the supernatant liquor obtained by centrifugation of the PPP preincubated with the polymer. In all cases, this time was found to be very close to the control time. In addition, to check that the increase in thrombin time was not due to an alteration of the fibrinogen, the coagulation times were also determined by reptilase, of PPP or of a fibrinogen solution incubated with the polymer. No significant difference was demonstratable between the reptilase times obtained in the presence or in the absence of polymer, as emerges from the results shown in FIG. 2. In this FIG. 2 is plotted the coagulation time in seconds as a function of the concentration of polymer suspension (expressed in number of $SO_3^-$/ml). The polymer suspension (0.1 ml) was incubated with 0.2 ml of PPP for 30 minutes at 37° C. Then 0.1 ml of thrombin at 9 U/ml (continuous curve) or of reptilase (curve in dashed lines) was added. The concentration of the thrombin was chosen to give a control time identical with reptilase, namely 20 seconds. The curves 1 correspond to PS—SO$_3$ and the curves 2 to a polymer according to the invention (PS—SO$_2$—Glu).

The curves obtained with the plasma, for different thrombin concentrations have also been transposed into amount of inactivated thrombin as a function of the amount of resin present in the test. In fact, to a first approximation, it may be considered that a prolonged thrombin time manifests the inactivation of an initial fraction of the thrombin and this fraction determined by comparing the coagulation time obtained with a curve of control times measured with the variable amounts of thrombin. FIG. 3 shows the curves thus obtained.

Curves 1 correspond to polymer PS—SO$_3$.

Curves 2 correspond to the polymer according to the invention PS—SO$_2$—Glu.

Curves 3 correspond to the supernatant liquors (PPP+PS—SO$_3$ and PPP+PS—SO$_2$—Glu).

The inactivated thrombin is plotted as ordinate in U/ml and the concentration of the suspension of polymer expressed in number of SO$_3^-$ groups/ml as abscissa. The amount of inactivated thrombin was evaluated from a calibration curve of control times (0.2 ml of PPP were incubated with 0.1 ml of MICHAELIS buffer at 37° C. 0.1 ml of thrombin—of variable concentration was added—and the coagulation time measured). The thrombin times, measured after incubation of PPP with polymer suspensions, were referred to this calibration curve, which enabled the concentration of active enzyme to be estimated, and hence the corresponding amount of inactivated thrombin.

Figure 3A:
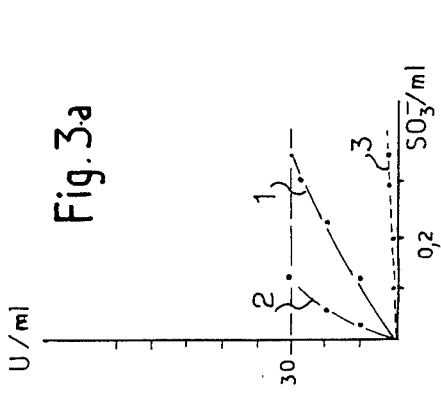
Figure 3B:
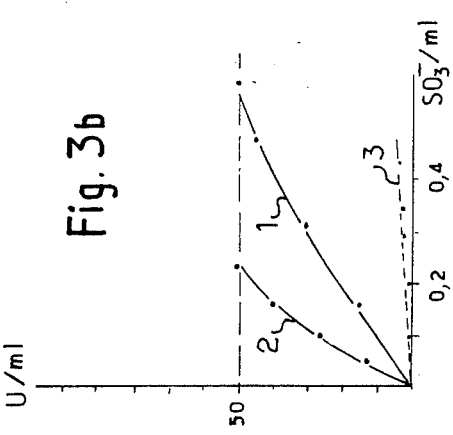
Figure 3C:
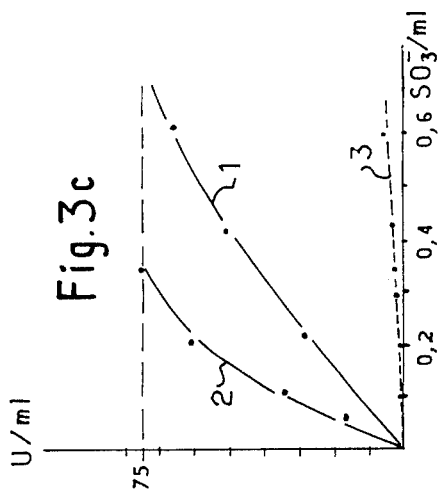

The curves shown in FIGS. 3a, 3b, 3c, show clearly that the porportion of inactivated thrombin increases with the amount of polymer present in the test. In addition, the measurements of thrombin times carried out on the supernatant liquors (compare curves 3) indicate that there was then no inactivation of the thrombin. These results show that the anticoagulant effect of the polymer is only exerted as long as the latter is present in the PPP.

The comparison of the thrombin times obtained under the same conditions for the PPP and the fibrinogen solution (cf. FIGS. 1 and 3) shows that the anticoagulant effect of the polymer is only manifested in the presence of a plasmatic factor absent from the fibrinogen solution.

The whole of these results suggests that the anticoagulant activity of these polymers is an antithrombic activivity involving antithrombin III as a plasmatic cofactor. In other words, these polymers are anticoagulant (heparin-like) substances.

V—ESTABLISHMENT OF THE GENERAL LAW OF VARIATION BETWEEN THE AMOUNT OF INACTIVATED THROMBIN AND THE AMOUNT OF PS—SO$_2$ AA PRESENT

The anticoagulant activity of the various samples was studied by the determination of the thrombin times PPP incubated with increasing amounts of polymer according to the invention. Previously, to verify that the anticoagulant activity of each resin was similar to that of the samples described in above paragraph IV, and in paragraph IX below, the reptilase times of PPP incubated with the polymer and the thrombin times of the fibrinogen solution incubated with the polymer were determined. They are all substantially equal to the corresponding control times (determined in the absence of polymer).

Figure 4:
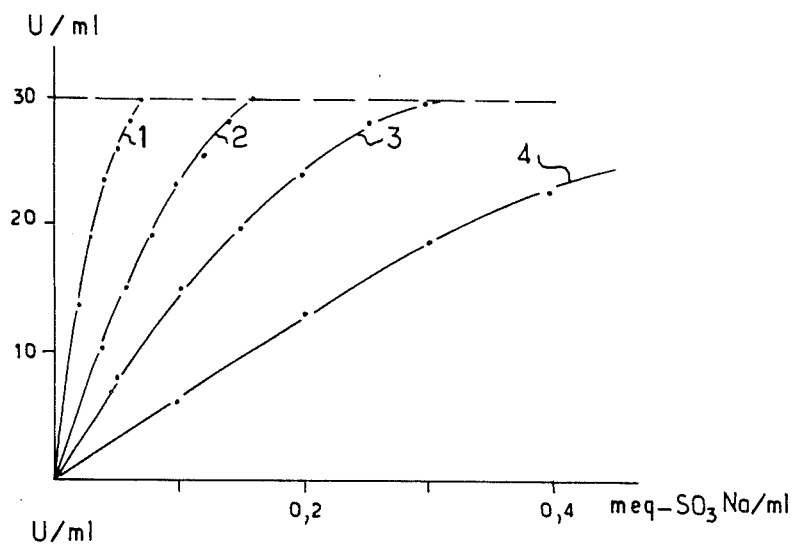

Prolongation of the thrombin time corresponding to the inactivation of a fraction of the initial thrombin, the comparison between a calibration curve and the coagulation time determined in the presence of a certain amount of resin, enables the amount of thrombin inactivated by this amount of resin present in the PPP to be determined. FIG. 4 shows the variation in the amount of thrombin inactivated as a function of the concentration of the resin suspension for a series of compounds containing proline in variable proportion with respect to the sulfonate groups. The concentration of the resin suspension is here expressed in milliequivalents of —SO$_3$Na groups per milliliter of suspension, which permits direct comparison of the effect of the proline groups and shows that the anticoagulant activity increases with the proportion of these groups.

FIG. 4 shows in fact the amount of thrombin inactivated as a function of the concentration of the suspension of PS—SO$_2$ polymer-proline (expressed in meq—SO$_3$Na/ml)

for 2.59 meq of proline per g of polymer: (curve 1)
for 2.09 meq of proline per g of polymer: (curve 2)
for 1.62 meq of proline per g of polymer: (curve 3)
for 0.93 meq of proline per g of polymer: (curve 4)

A same series of curves was obtained for each amino acid.

Figure 5:
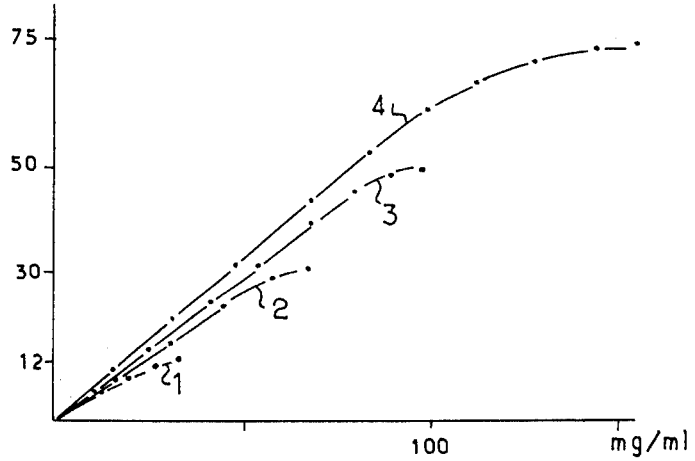

FIG. 5 shows the variation in the amount of thrombin inactivated as ordinate, as a function of the polymer concentration (in mg/ml) for a resin bearing glutamic acid groups and for four thrombin concentrations:

12 U/ml (curve 1)
30 U/ml (curve 2)
50 U/ml (curve 3)
75 U/ml (curve 4)

Figure 6:
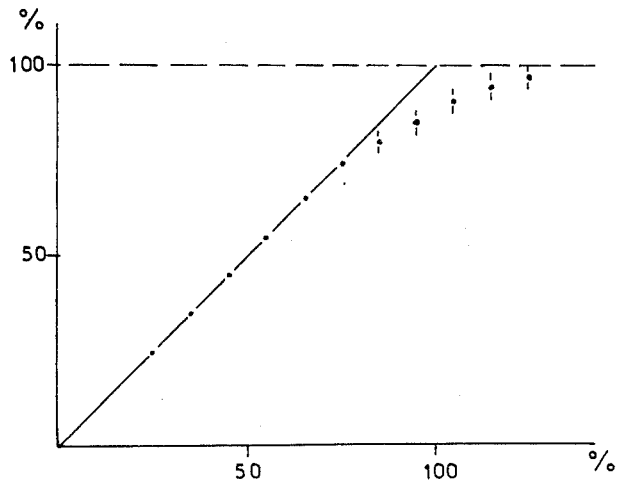

The same curves were established for all the other products according to the invention, which were prepared, and it was observed that the law of variation was the same in all cases. This variation is firstly linear, which shows that the amount of thrombin inactivated is proportional to the amount of polymer present whatever the concentration of thrombin used. However to achieve 100% inactivation, an excess of polymer is always necessary. Extrapolation of the tangent at the origin enables for each polymer, the determination of the amount of resin theoretically necessary to completely inactivate a certain amount of thrombin. This results clearly from FIG. 6 wherein the magnitudes have been plotted in reduced coordinates: as ordinate, the thrombin inactivated as % of the total, and as abscissa the amount of polymer in % of the amount theoretically necessary to inactivate all the thrombin present.

Figure 7:
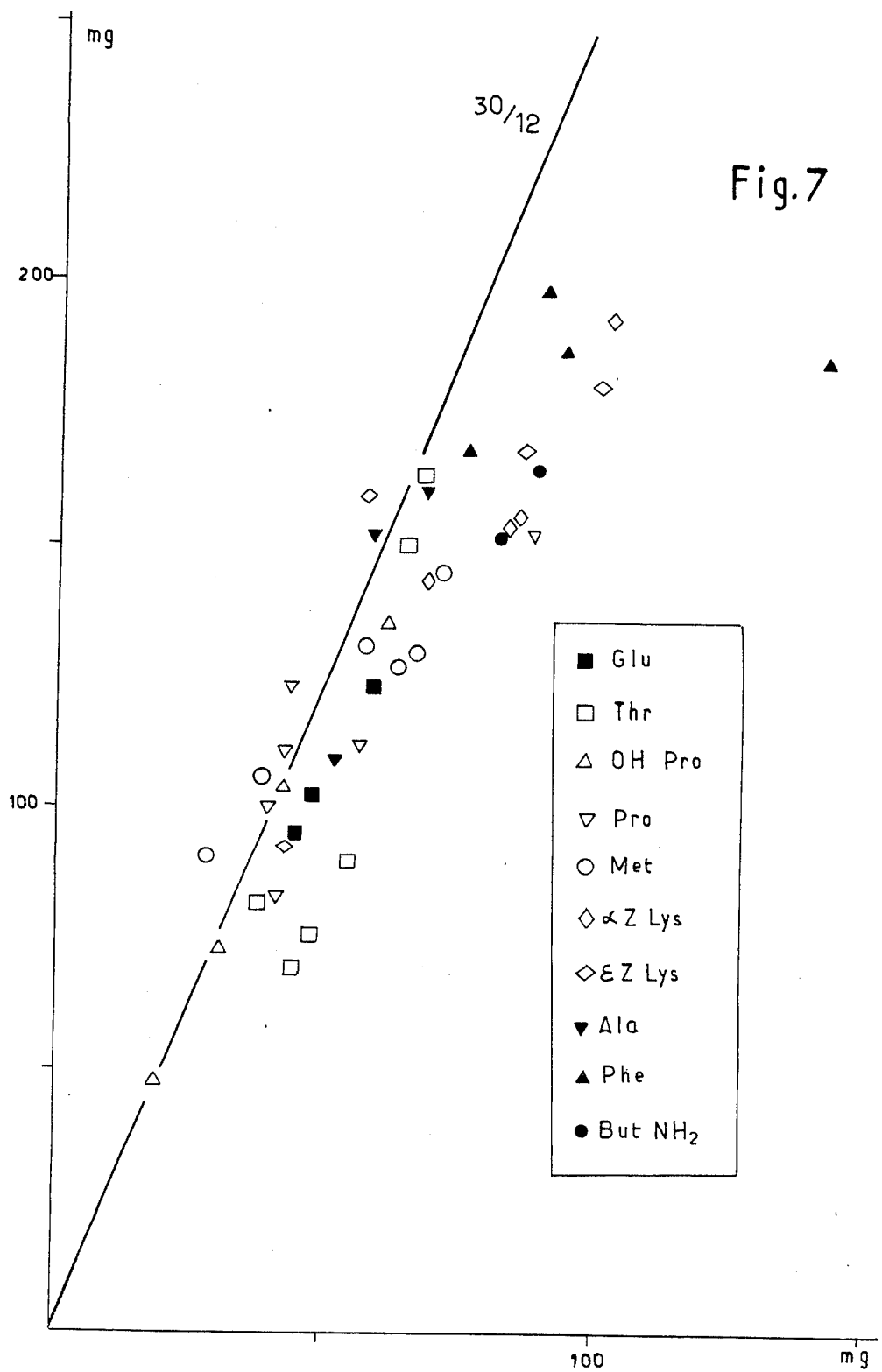
Figure 8:
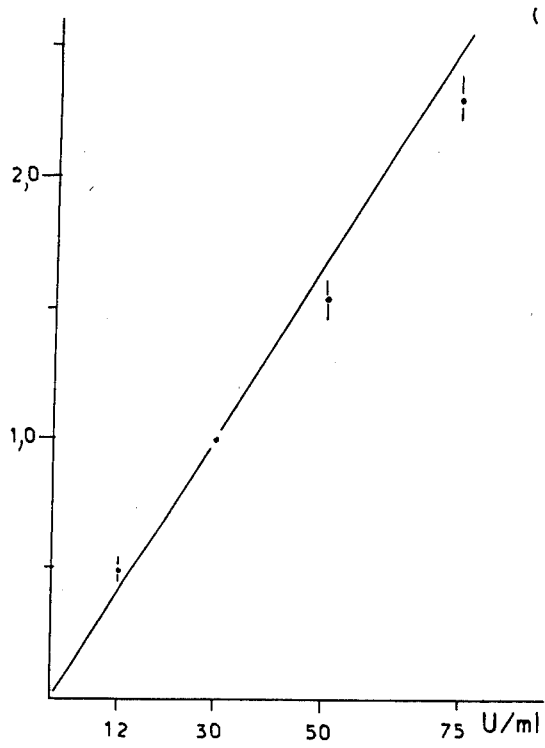

FIG. 7 enables the generally of this law of proportionality to be checked. In fact, each point corresponds here to the amount of polymer necessary to inactivate 30 units of thrombin as a function of the amount of the same polymer necessary to inactivate 12 units of thrombin. All these points are substantially aligned and very close to the slope line 30/12 corresponding to proportionality, which shows that the variation relationship is valid for all the amino acids studied. It is then possible to determine an activity for each resin as the inverse of the amount of resin necessary to inactivate 30 units of thrombin. By using this value as a reference, it is then possible to show that the proportionality law is valid for thrombin concentrations varying from 12 to 75 units/ml, as shown in FIG. 8 wherein there is plotted as abscissa the concentration of the thrombin and as ordinate the ratio:
Polymer necessary to inactivate X units of thrombin
Polymer necessary to inactivate 30 units of thrombin
Summarizing, it emerges clearly from FIGS. 7 and 8:
that the inactivation of all the thrombin present is achieved provided that a sufficient amount of polymer according to the invention is added
that the same inactivation law is followed by all the products according to the invention, whatever the amino acid (AA) and whatever the amount of this AA present in the resin.

VI—CASE OF DIAMINO ACIDS (LYSINE)

Figure 9:
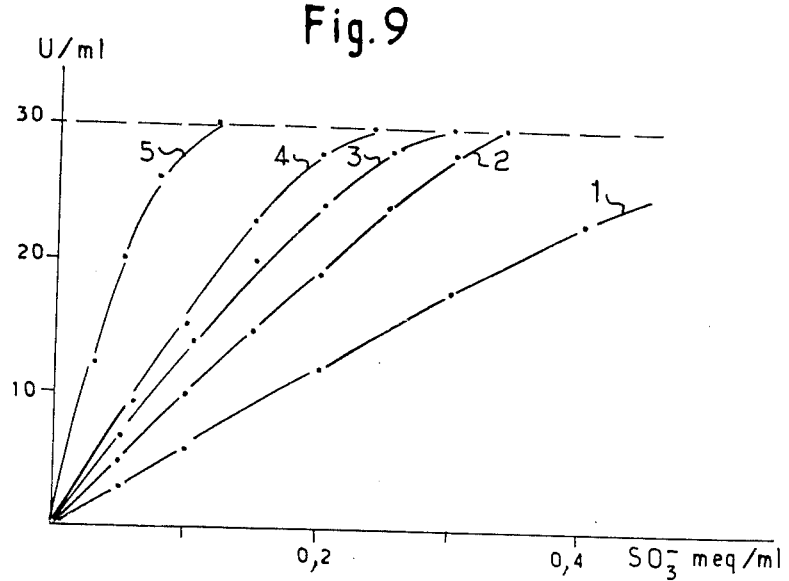

In FIG. 9 are shown, the graphs of the variation of the amount of thrombin inactivated (as ordinate in U/ml) as a function of the amount of resin present in the test.
The Curve 1 relates to the polymer PS—SO$_2$—Lysine
Curve 2 relates to the sulfonated PS—SO$_3$ polymer
Curve 3 relates to the PS—SO$_2$-Proline polymer
Curve 4 relates to the PS—SO$_2$—αZ Lysine polymer
Curve 5 relates to the PS—SO$_2$-Glutamic polymer Z being the electroattractor benzyloxycarbonyl group.

The amount of resin being expressed in concentration of sulfonate groups per milliliter of suspension for all the resins, the curves above that of a resin only containing sulfonate groups (curve 2) indicate that the corresponding amino acid confers on the resin to which it is fixed, an additional anticoagulant acitivity with respect to that of its sulfonate groups alone. This is the case for all amino acids except lysine. In this case on the contrary, the curve is below that of a resin only containing sulfonate groups (PS—SO$_3$), that is to say the presence of lysine on the resin reverts to "neutralising" a part of the anticoagulant activity of the sulfonate sites. This approaches the inhibiting effect, described in paragraph IX below, observed with polylysine whose amino sites of the side chains, protonised to pH 7.35, neutralise the negative sites, notably sulfonates, of a PS—SO$_3$ resin, or PS—SO$_2$AA, or of heparin.

On the other hand, when an amine function of the lysine is blocked (curve 4), this neutralisation is no longer possible and the polymer fully recovers its properties.

VII—CASE OF PS—CH$_2$—AA RESINS (THE AMINO ACID IS LINKED TO THE MACROMOLECULAR CHAINS THROUGH THE —CH$_2$— BRIDGE)

This study was based on three resins containing respectively proline, hydroxyproline and alanine (cf. Table I: compounds 11, 12 and 13). In each case, the thrombin times of PPP incubated with variable amounts of resin were determined. They were still found to be substantially equal to the control time, whatever the amount of resin present.

VIII—ESTIMATION OF THE ACTIVITY OF EACH TYPE OF SUBSTITUENT ITSELF

Starting from the activity of each resin defined previously with respect to 30 thrombin units, it is possible to deduce the activity with respect to a thrombin unit (cf. Table II). If the effects of different substituents of the resin are additive, the activity "a" may be expressed by the following relationship (1):

$$a(C_{SO_3^-} + C_{AA}) = (a_{SO_3^-} X C_{SO_3^-}) + (a_{AA} X C_{AA}) \quad (1)$$

where $a_{SO_3^-}$ and $a_{AA}$ are the activities respectively of a sulfonate group and of an —SO$_2$ amino acid group, $C_{SO_3^-}$ and $C_{AA}$ being their respective concentrations.

Figure 10:
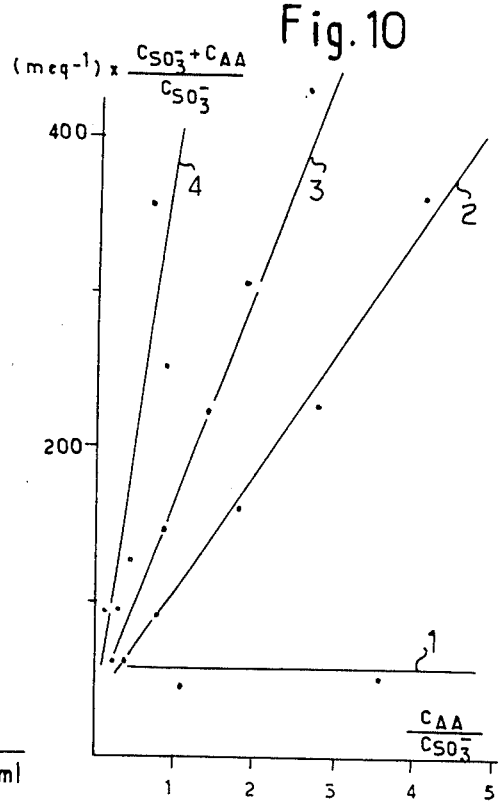

FIG. 10 shows the curves obtained by plotting the activity of the resin "a", multiplied by the ratio of the total number of sites and of the number of sulfonate sites $$\frac{C_{SO_3^-} + C_{AA}}{C_{SO_3^-}} \text{ (as ordinates)}$$

as a function of the ratio of the numbers of —SO$_2$— amino acid and sulfonate sites $$\frac{C_{AA}}{C_{SO_3^-}} \text{ (as abscissae)}$$

These curves have a common ordinate at the origin equal to the activity of a sulfonate group ($a_{SO_3^-}$) and slopes equal to the activities of the amino acid groups ($a_{AA}$).
The curve 1 corresponds to the polymer PS—SO$_2$—But—NH$_2$
The curve 2 corresponds to the polymers
PS—SO$_2$—alanine
PS—SO$_2$phenylalanine
The curve 3 corresponds to the polymers
PS—SO$_2$—Z lysine
PS—SO$_2$—hydroxyproline
PS—SO$_2$—methionine
PS—SO$_2$—proline
PS—SO$_2$—threonine
The curve 4 corresponds to the polymer PS—SO$_2$—Glutamic acid.

The activities of the various types of substitutents are regrouped in Table II and Table III below:

TABLE II

| A- Support polymer: Polystyrene | | | |
|---|---|---|---|
| Substituent | Coefficient of activity in (meq)$^{-1}$ u Th$^{-1}$ | Substituent | Coefficient |
| —SO$_2$ ASP | 550 | SO$_2$ZLys | 130 |
| —SO$_2$ Glu | 370 | | |
| —SO$_2$ ε-amino-caproic | 200 to 300 | —SO$_2$—Ala<br>—SO$_2$—Phe | comprised between 60–80 |
| —SO$_2$β-alanine | | | |
| —SO$_2$OH Prol | comprised between 120 and 150 | —SO$_3'$ | 60 |
| —SO$_2$Prol | | SO$_2$But NH$_2$ | 0 |
| —SO$_2$Met | | | |
| —SO$_2$Thr | | | |

It is seen clearly that:
the activity of butylamine is nil, which seems to indicate that the sulfamide group alone is not sufficient to confer an antithrombic activity on the resin and that the substituents devoid of acid carboxylic function have no effect on this activity.
The alanine and phenylalanine groups have an activity comprises between 60 and 80 meq$^{-1}$, close to that of the sulfonate group, 60 meq$^{-1}$, which could indicate that a hydrocarbon side chain has practically no role and that the activity of the carboxylic function of the amino acid is of the same order of magnitude as that of the sulfonate group. The slight difference between alanine and phenylalanine is probably explained by the more marked hydrophobic character of the side chain of phenylalanine with respect to alanine.

Lysine whose amino function of the side chain is substituted by an electron attractor group (group Z) has a positive activity, but difficult to define with accuracy to the extent that it has not been possible to synthesize resins containing more amino acid groups than sulfonate groups. The same problem occurs for lysine, but in this case, the activity, also poorly defined, is negative.

The amino acids whose side chain contains a heteroatom, such as hydroxyproline, threonine and methionine, have a higher activity comprised between 120 and 150 meq$^{-1}$.

Proline seems also to be attachable to this group. It must be noted that two of these amino acids, proline and and hydroxyproline, fixed to the polystyrene by a methylene group (resin PS—CH$_2$AA) do not confer any anticoagulant activity on the material.

The dicarboxylic acids, like glutamic acid or aspartic acid, have a higher activity than all the other α-amino acids, probably connected with their two carboxylic functions.

The amino acids in which the amine function and the carboxylic function are separated by several methylene groups, such as for example alanine, or ε-aminocaproic acid, have an activity which is all the higher as the as the number of methylene groups is greater, probably associated with a "arm" effect of the carbon chain making the carboxylic function more accessible.

All of these results enable a certain number of conclusions to be drawn. The sulfamide group is not sufficient for anticoagulant activity to exist; however, it seems that it is necessary since the resins PS—CH$_2$—AA have no activity.

The sulfonate groups, on the other hand, are sufficient for anticoagulant activity to exist, but the latter is slight to very slight, at the most 15% of that of heparin, when all the sites of the polymer (PS) are substituted by SO$_3^-$ groups.

On the contrary, when the macromolecular chain bears both sulfonate groups, amino acids fixed through a sulfamide and/or amide bridge and the amino acids have a favorable side chain, the anticoagulant activity of the substance may be very great.

TABLE III

B - Support polymer: Dextran
Study of the coagulation time as a function of the nature of R$_3$ and the amount of SO$_3^-$ in the polymer

| | Nature of R$_3$ | Meq of SO$_3^-$ in the initial polymer solution necessary to have the thrombin time of 20 seconds (concentration of thrombin 30 U/ml) |
|---|---|---|
| 1 | —CH$_2$—⟨O⟩— | 17.10$^{-3}$ |
| 2 | —CH$_2$CO—NH—CH$_2$—⟨O⟩— | 2.5.10$^{-3}$ |
| 3 | —CH$_2$—C—NH—CH$_2$—<br>‖<br>O | 200.10$^{-3}$ |

Control without the polymer: 7 seconds.

It results from comparison of these three products that it is the product no. 2 which proves to be the best: time of 20 seconds for a concentration of only 2.5×10$^{-3}$ in meq of SO$_3^-$.

For very finely ground products there have thus been found, from measurement of thrombin times, the following activity coefficients:

| Substituent | Activity coefficient |
|---|---|
| —CH$_2$CO—NH—CH$_2$—⟨O⟩—SO$_3^-$ | 12.10$^3$ meq$^{-1}$ u Th$^{-1}$ |
| —CH$_2$CO—Threonine | 36.10$^3$ meq$^{-1}$ u Th$^{-1}$ |

IX—OTHER PROPERTIES SIMILAR TO HEPARIN OF THE COMPOUNDS ACCORDING TO THE INVENTION

A—Study of the action of inhibitors

Heparin inhibitors (polybrene and polylysine) can completely inhibit the anticoagulant effect of the polymers according to the invention.

The results are illustrated in the appended FIG. 11 (in which the thrombin time in seconds is plotted as ordinate, and the concentration of inhibitor in mg/ml as abscissa). The experimental system is as follows: polymer suspension (0.1 ml) is incubated with 0.2 ml of PPP and 0.1 ml of an inhibitor solution (of variable concentration) for 30 minutes at 37° C. 0.1 ml of thrombin (12 U/ml) is then added and the coagulation time is measured. The graphs 1 relate to polybrene and the graphs 2 to polylysine.

Figure 11B:
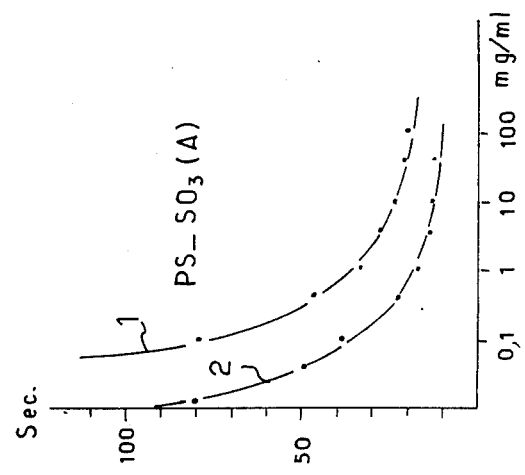
Figure 11A:
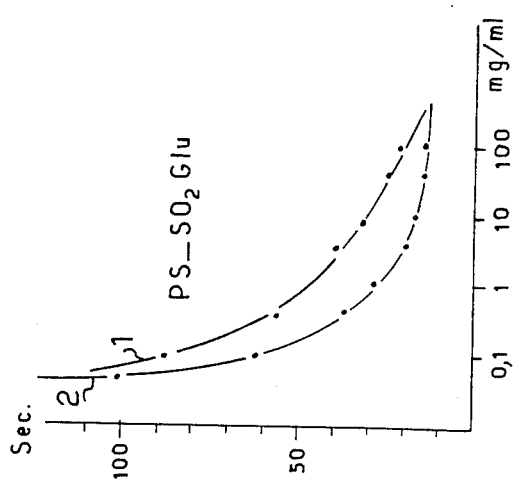

FIG. 11a shows the results obtained with PS—SO$_2$-Glu and FIG. 11b those obtained with the polymer PS—SO$_3$. In FIG. 11 it is seen that this inhibition is only complete provided that there is an excess of positive charge of the inhibitor with respect to the negative charges of the polymer, whereas for heparin it is complete without excess. It is also to be noted that a greater excess is necessary with polybrene than with polylysine. These results indicate that a large proportion of the accessible negative sites of the resin, are involved in its anticoagulant activity.

B—Study of the inactivation of thrombin by the polymers in the presence or in the absence of antithrombin III This second study was done in two series:
(a) the polymers were incubated with thrombin or successively with thrombin and polybrene.
(b) the polymers were incubated with thrombin and with antithrombin III or successively with thrombin, with antithrombin III and with polybrene. In all cases, a mixture was then centrifuged and the supernatant liquor was added to PPP or to a solution of fibrinogen. The coagulation time was then measured (cf. Table IV below). The results obtained show that in the absence of antithrombin III, the thrombin is inactivated reversibly by the polymer; its activity reappears in the presence of polybrene. On the other hand, in the presence of antithrombin III, the inactivation of the thrombin by the polymer is irreversible, as is the case with heparin.

TABLE IV
STUDY OF THE INACTIVATION OF THROMBIN BY THE POLYMERS IN THE PRESENCE OR THE ABSENCE OF ANTITHROMBIN III

| Sample | | Thrombin + buffer (a)* | Thrombin + polybrene (b)* | Thrombin + antithrombin + buffer (c)* | Thrombin + antithrombin + polybrene (d)* |
|---|---|---|---|---|---|
| PS—SO$_3$ | PPP | 70 | 45 | 250 | 64 |
| | Fibrinogen solution | 110 | 44 | 300 | 60 |
| PS—SO$_2$Glu | PPP | 112 | 45 | 300 | 65 |
| | Fibrinogen solution | 150 | 47 | 360 | 62 |

*coagulation time in seconds

Experimental system: a suspension (0.2 ml) of polymer in the buffer was incubated at 0° C. with 0.2 ml of thrombin at 5 units/ml (a) (b) or with 0.016 ml of antithrombin III with 25 units/ml and 0.2 ml of thrombin with 5 units/ml (c) (d). After 5 minutes, 0.2 ml of buffer (a) (c) or 0.2 ml of a polybrene solution (40 mg/ml in buffer) (b) (d) were added. After 5 minutes at 0° C., the suspension was centrifuged and 0.3 ml of supernatant liquor were added to 0.2 ml of PPP or 0.2 ml of fibrinogen solution at 37° C. The coagulation time (in seconds) was then measured. Control time: 45 seconds in the absence of antithrombin III and 60 seconds in the presence of antithrombin III.

It results from the foregoing description that the products according to the present invention have very marked anticoagulant activity. If as support polymer a noncrosslinked polymer is selected, soluble products with anticoagulant action are obtained, for pharmaceutical use proper, and if as support polymer a crosslinked polymer is selected, insoluble products with anticoagulant action are obtained, for medical or surgical use for example. This anticoagulant activity in the solid state is relatively high: it is of the same order of magnitude as that of heparin itself fixed by covalent bonds to polymeric materials—but contrary to the latter, the products according to the invention are remarkably stable.

Thus as emerges from the foregoing, the invention is in no way limited to those of its types of application, embodiments and uses which have just been described more explicitly it encompasses, on the contrary, all modifications which may occur to the technician skilled in the art, without departing from the framework, or the scope, of the present invention.

We claim:

1. A substituted synthetic water soluble or water insoluble polymer that has blood anticoagulating properties of natural heparin, said polymer comprising
   a polymer selected from the group consisting of polystyrene, dextran, and styrene-divinylbenzene copolymer on which there is fixed groups X, V and Y, wherein:
   X is H, —SO$_3$R$_1$ or —R$_3$SO$_3$R$_1$,
   Y is H, —SO$_2$R$_2$ or —R$_3$SO$_2$—R$_2$
   V is H, or —CH$_2$—CO—NH—CHR—COOH, with the provision that at least one of X, Y and V is other than H,
   R is the side chain of an amino acid,
   R$_1$ is a hydrogen atom or a pharmaceutically acceptable metal salt,
   R$_2$ is a single amino acid connected to the —SO$_2$ bridge through its amine function,
   R$_3$ is —CH$_2$—CO—NH—R$_4$,
   R$_4$ is alkyl, phenyl or, benzyl and further when X is —SO$_3$R$_1$, then at least one of Y or V is other than H and where V is —CH$_2$—CO—NH—CHR—COOH, at least one of X or Y is other than H; and X, Y, and V are as defined above.

2. The polymers of claim 1 which is a copolymer.

3. The polymer of claim 1 wherein when X is —SO$_3$R$_1$ or —R$_3$SO$_3$R$_1$, then at least one of Y or V is other than H.

4. The polymer of claim 1 wherein when X is —R$_3$SO$_3$R$_1$, then Y and V are H.

5. The polymer of claim 1 wherein the amino acids have at least one free carboxylic function.

6. The polymer of claim 5 wherein the amino acid is a dicarboxylic acid.

7. The polymer of claim 1 wherein the amino acids are selected from the group which consists of: glutamic acid, aspartic acid, methionine, cysteine, cysteic acid, proline, hydroxyproline, threonine, serine, tyrosine, alanine, phenylalanine, valine, leucine, benzyloxycarbonyl-lysine, tertiobutyloxycarbonyl-lysine, 6-aminocaproic acid, beta-alanine 4-amino-n-butyric acid and 5-amino-n-valeric acid.

8. The polymer of claim 1 wherein the amino acid is not substituted.

9. The polymer of claim 1 wherein the amino acid has more than one amino function, all except one being blocked by a physiologically acceptable blocking group.

10. The polymer of claim 9 wherein the blocking group is selected from the group consisting of a benzyloxy-carbonyl or a tertiobutyloxycarbonyl group.

11. The polymer of claim 1 wherein the backbone polymer is polystyrene.

12. The polymer of claim 1 wherein the functional groups on the backbone comprises about 1.37 meq per gram of hydroxyproline and about 2.16 meq of sulfonate per gram of polymer.

13. The polymer of claim 1 wherein the polymer is polystyrene which is not cross-linked and X is —SO$_3$R$_1$, Y is —SO$_2$R$_2$, and V is H.

14. The polymer of claim 1 wherein

15. A pharmaceutical composition having anticoagulant properties comprising a biologically acceptable carrier and a biologically effective amount of a polymer soluble in water or biological fluids defined in claim 1.

16. The pharmaceutical composition according to claim 15 wherein the polymer is a polystrene.

17. A substituted synthetic water soluble polysaccharide that has the blood anticoagulant properties of natural heparin, which polysaccharide comprises
a dextran on which there is fixed the groups X, V and Y, wherein:
X is H, $-SO_3R_1$ or $-R_3SO_3R_1$,
Y is H, $-SO_2R_2$ or $-R_3SO_2-R_2$
V is H, or $-CH_2-CO-NH-CHR-COOH$, with the provision that at least one of X, Y and V is other than H,
R is the side chain of an amino acid having at least one free carboxylic acid group,
$R_1$ is a hydrogen atom or a pharmaceutically acceptable metal salt,
$R_2$ is a single amino acid connected to the $-SO_2$ bridge through its amine function,
$R_3$ is $-CH_2-CO-NH-R_4$,
$R_4$ is alkyl, phenyl or benzyl, and further when X is $-SO_3R_1$, then at least one of Y or V is other than H and where V is $-CH_2-CO-NH-CHR-COOH$, at least one of X or Y is other than H; and X, Y, and V are as defined above.

18. The polysaccharide of claim 17 wherein the amino acid is glutamic acid.

19. The polysaccharide of claim 17 wherein X is $R_3SO_3R_1$, V is $-CH_2-CO-NH-CHR-COOH$, and Y is H.

20. The polysaccharide of claim 19 wherein

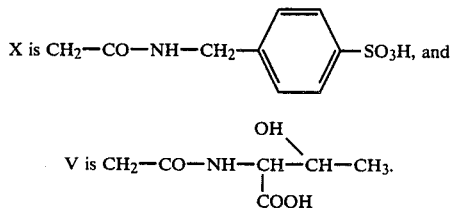

21. The polysaccharide of claim 17 wherein X is $-SO_3R_1$, V is $CH-CO-NH-CHR-COOH$, and Y is H.

22. The polymer of claim 21 wherein

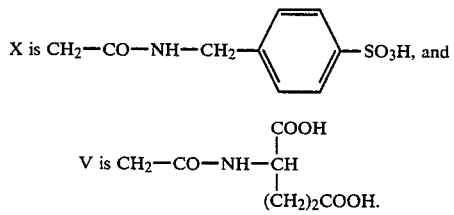

23. A pharmaceutical composition having anticoagulating properties comprising a biologically acceptable carrier and a biologically effective amount of a polymer soluble in water or biological fluids defined in claim 17.

24. A substitute synthetic water-insoluble polystyrene having the blood anticoagulant properties of natural heparin, which comprises a polystyrene on which there is fixed the groups X and Y, wherein:
X is $-SO_3R_1$, and
Y is $-SO_2R_2$,
wherein:
$R_1$ *is a hydrogen atom or a pharmaceutically acceptable metal salt, and*
$R_2$ is a single amino acid which is connected to the $-SO_2$ bridge through its amine function.

25. The polystyrene of claim 24 wherein the amino acid is glutamic acid.

26. A substituted water-insoluble polystyrene having the blood anticoagulant properties of natural heparin, which comprises a polystyrene on which there is fixed the groups X and Y, wherein
X is $-SO_3R_1$, and
Y is $-SO_2R_2$,
wherein:
$R_1$ is a hydrogen atom or a pharmaceutically acceptable metal salt, and
$R_2$ is a hydroxyproline which is connected to the $-SO_2$ bridge through its amine function.

27. A substituted synthetic water-insoluble polysaccharide that has the blood anticoagulant properties of natural heparin, which polysaccharide comprises
a dextran on which there is fixed the groups X, V and Y, wherein:
X is H, $-SO_3R_1$ or $-R_3SO_3R_1$,
Y is H, $-SO_2R_2$ or $-R_3SO_2-R_2$
V is H, or $-CH_2-CO-NH-CHR-COOH$, with the provision that at least one of X, Y and V is other than H,
R is the side chain of an amino acid,
$R_1$ is a hydrogen atom or pharmaceutically acceptable metal salt,
$R_2$ is a single amino acid connected to the $-SO_2$ bridge through its amine function,
$R_3$ is $-CH_2-CO-NH-R_4$,
$R_4$ is alkyl, phenyl or benzyl, and further when X is $-SO_3R_1$, then at least one of Y or V is other than H, and where V is present, at least one of X or Y is other than H; and X, Y, and V are as defined above.

28. The polysaccharide of claim 27 wherein the polyglucoside is crosslinked.

29. The polymer of claim 27 wherein the polymer is a dextran and X is $-R_3SO_3R_1$, V is $-CH_2-CO-NH-CHR-COOH$, and Y is H.

30. The polymer of claim 27 wherein X is $-SO_3R_1$, V is $-CH_2-CO-NH-CHR-COOH$, and Y is H.

* * * * *